(12) United States Patent
Farrell et al.

(10) Patent No.: US 8,329,219 B2
(45) Date of Patent: Dec. 11, 2012

(54) METHODS FOR PRODUCING ECM-BASED BIOMATERIALS

(75) Inventors: Laura-Lee Farrell, Maplewood, MN (US); Chad E. Johnson, West Lafayette, IN (US)

(73) Assignees: Cook Biotech Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 228 days.

(21) Appl. No.: 12/644,607

(22) Filed: Dec. 22, 2009

(65) Prior Publication Data

US 2011/0150998 A1    Jun. 23, 2011

(51) Int. Cl.
*A61K 9/14* (2006.01)
*B29C 41/04* (2006.01)
*A61P 17/02* (2006.01)

(52) U.S. Cl. .................. 424/484; 424/130.1; 424/423; 424/550; 514/12

(58) Field of Classification Search ............... 424/484, 424/423, 550
See application file for complete search history.

(56) References Cited

U.S. PATENT DOCUMENTS

| | | | |
|---|---|---|---|
| 3,850,368 A | 11/1974 | Boeckeler | |
| 3,881,878 A | 5/1975 | Maruta et al. | |
| 4,223,101 A | 9/1980 | Fine et al. | |
| 4,260,009 A | 4/1981 | Noble | |
| 4,323,454 A | 4/1982 | Fritzsche et al. | |
| 4,517,138 A | 5/1985 | Rawlings et al. | |
| 4,552,707 A | 11/1985 | How | |
| 4,586,960 A | 5/1986 | Iizuka et al. | |
| 4,610,693 A | 9/1986 | Niwa et al. | |
| 4,801,299 A * | 1/1989 | Brendel et al. ............... 623/1.47 | |
| 4,822,692 A | 4/1989 | Koehler | |
| 4,902,508 A | 2/1990 | Badylak et al. | |
| 4,956,178 A | 9/1990 | Badylak et al. | |
| 5,122,554 A | 6/1992 | Allen | |
| 5,234,754 A | 8/1993 | Bache | |
| 5,266,325 A | 11/1993 | Kuzma et al. | |
| 5,281,422 A | 1/1994 | Badylak et al. | |
| 5,292,515 A | 3/1994 | Moro et al. | |
| 5,295,528 A | 3/1994 | Diyecha et al. | |
| 5,322,648 A | 6/1994 | Dapper | |
| 5,372,821 A | 12/1994 | Badylak et al. | |
| 5,423,634 A | 6/1995 | Fujita et al. | |
| 5,436,384 A | 7/1995 | Grant et al. | |
| 5,456,693 A | 10/1995 | Conston et al. | |
| 5,487,895 A | 1/1996 | Dapper et al. | |
| 5,498,383 A | 3/1996 | Marple et al. | |
| 5,554,389 A | 9/1996 | Badylak et al. | |
| 5,605,693 A | 2/1997 | Seare, Jr. | |
| 5,786,898 A | 7/1998 | Fitzpatrick | |
| 5,906,836 A | 5/1999 | Panaroni et al. | |
| 5,980,792 A | 11/1999 | Chamlee | |
| 6,001,440 A | 12/1999 | Miyamoto et al. | |
| 6,099,567 A | 8/2000 | Badylak et al. | |
| 6,136,452 A | 10/2000 | Munir et al. | |
| 6,206,931 B1 | 3/2001 | Cook et al. | |
| 6,225,246 B1 | 5/2001 | Darcovich | |
| 6,350,710 B1 | 2/2002 | Jonas et al. | |
| 6,361,797 B1 | 3/2002 | Kuzma et al. | |
| 6,554,054 B2 | 4/2003 | Noble | |
| 6,635,213 B1 | 10/2003 | Carlström | |
| 6,641,760 B2 | 11/2003 | Matsuo et al. | |
| 6,773,550 B2 | 8/2004 | Nygärd et al. | |
| 6,787,090 B2 | 9/2004 | Dalton et al. | |
| 6,913,716 B2 | 7/2005 | Lee et al. | |
| 6,969,480 B2 * | 11/2005 | Dalton et al. ................. 264/255 |
| 7,052,710 B2 | 5/2006 | Giordano et al. | |
| 7,387,604 B2 | 6/2008 | Case et al. | |
| 2003/0108697 A1 | 6/2003 | Carlstrom et al. | |
| 2004/0044397 A1 | 3/2004 | Stinson | |
| 2005/0281701 A1 | 12/2005 | Lynch et al. | |
| 2006/0016332 A1 | 1/2006 | Ma et al. | |
| 2006/0055077 A1 | 3/2006 | Heikkila | |
| 2006/0184149 A1 | 8/2006 | Kasai et al. | |
| 2006/0222844 A1 | 10/2006 | Stinson | |
| 2007/0003749 A1 | 1/2007 | Asgari | |
| 2007/0026040 A1 | 2/2007 | Crawley et al. | |
| 2007/0098755 A1 * | 5/2007 | Patel et al. ..................... 424/423 |
| 2007/0207186 A1 | 9/2007 | Scanlon et al. | |
| 2007/0221500 A1 | 9/2007 | Hausselt et al. | |
| 2007/0264481 A1 | 11/2007 | DeSimone et al. | |
| 2007/0292750 A1 | 12/2007 | Beard | |
| 2008/0004657 A1 * | 1/2008 | Obermiller et al. ........... 606/213 |
| 2008/0026032 A1 | 1/2008 | Zubery et al. | |
| 2008/0075937 A1 | 3/2008 | Wada et al. | |
| 2008/0107750 A1 | 5/2008 | Hodde et al. | |
| 2008/0178535 A1 | 7/2008 | Wan | |
| 2008/0286268 A1 * | 11/2008 | Johnson ..................... 424/130.1 |
| 2009/0317469 A1 | 12/2009 | Johnson et al. | |
| 2009/0318934 A1 | 12/2009 | Johnson et al. | |
| 2009/0326577 A1 | 12/2009 | Johnson et al. | |

FOREIGN PATENT DOCUMENTS

| | | |
|---|---|---|
| WO | WO 95/05162 | 2/1995 |
| WO | WO 01/85417 | 11/2001 |
| WO | WO 2004/071736 | 8/2004 |
| WO | WO2007/122232 | * 11/2007 |
| WO | WO 2008/027989 | 3/2008 |

* cited by examiner

*Primary Examiner* — Fereydoun G Sajjadi
*Assistant Examiner* — Anna Falkowitz
(74) *Attorney, Agent, or Firm* — Brinks Hofer Gilson & Lione

(57) ABSTRACT

A method for forming an extracellular matrix material (ECM) material includes providing at least an ECM composition containing ECM particles varying in their capacity for migration through a fluid medium, including at least one population of expanded ECM particles. The ECM composition is combined in a fluid medium to form a flowable ECM composition. The flowable ECM composition is subjected to a centrifugal force in a mold for a period of time sufficient to distribute the ECM particles according to differences in their physical characteristics. The ECM composition is dried to form a dried ECM material having a density gradient extending from a less dense region to a more dense region. The dried ECM material may formed as a porous, substantially acellular ECM material expandable in an aqueous fluid environment by at least 100% in volume.

14 Claims, No Drawings

METHODS FOR PRODUCING ECM-BASED BIOMATERIALS

TECHNICAL FIELD

The present invention relates generally to compositions and methods for producing extracellular matrix (ECM)-based materials, including medical devices prepared therefrom, having improved mechanical and/or compositional properties.

BACKGROUND

Biomaterials have been used in a variety of medical applications, including joint repair and replacement; periodontal reconstruction; repair or replacement of injured, diseased or malformed bones and tissues; wound healing; and the treatment of burns and diabetic ulcers. Extracellular matrix (ECM) materials, including those derived from submucosa and other tissues, are known tissue graft materials used in these medical applications. See, e.g., U.S. Pat. Nos. 4,902,508, 4,956,178, 5,281,422, 5,372,821, 5,554,389, 6,099,567, and 6,206,931. These materials typically are derived from a variety of biological sources including, for example, small intestine, stomach, urinary bladder, skin, pericardium, dura mater, fascia, and the like.

Submucosa and other ECM-based materials have been shown to include a variety of components other than collagen that can contribute to the bioactivity of the materials and to their value in medical grafting and other uses. As examples, ECM materials can include growth factors, cell adhesion proteins, proteoglycans, nucleic acids, and lipids. Depending on the needs for their use, ECM materials may be subjected to various manipulations in their manufacture, which can deplete an ECM of these components and alter its physical properties, including integrity and strength. Ideally, an ECM-based medical device should have sufficient integrity and strength to facilitate stable engraftment via suturing to suitable supporting structures that are designed to reduce the risk of inappropriate device migration in a body. Given that manipulation of ECM-based materials may result in a spongy material that is difficult to suture or attach to supporting structures, there is a need for improved ECM-based materials and medical products, as well as methods for preparing and using the same.

SUMMARY

In one embodiment, a method for forming an extracellular matrix material (ECM) material includes providing an ECM composition containing ECM particles differing in their ability to migrate through a fluid medium, such as an aqueous liquid medium, when subjected to a centrifugal force. The ECM particles can differ in their size, density, shape, or combinations thereof, relative to one another, and can include a population of volumetrically expanded ECM particles. The ECM particles in the composition are combined in a fluid medium to form a flowable ECM composition. The flowable ECM composition is introduced to a mold and subjected to a centrifugal force about an axis of rotation for a period of time sufficient to distribute the ECM particles in the mold according to size, density, shape, or combinations thereof. The contents in the mold are processed to form a dried ECM material having a shape defined by the mold. The resulting dried ECM material can be characterized by a density gradient extending from a less dense region to a more dense region.

In certain embodiments, the resulting dried ECM material can be characterized by a central longitudinal axis at the axis of rotation and by outer surfaces, such that the ECM particles establish a density gradient in the ECM material. In one form, the dried ECM material can be characterized by an outer density near an outer surface that is greater than an inner density of the dried ECM material toward the central longitudinal axis. In another form, the dried ECM material can be characterized by an outer density near an outer surface that is less than an inner density of the dried ECM material toward the central longitudinal axis. Conditions in the preparation such as the size, density, and/or shape of the ECM particles, and/or the specific gravity of a liquid medium used to prepare the suspension of ECM particles, can be varied to achieve the various forms of the final, dried ECM material. Further, differentially-migrating populations of ECM particles included in the flowable ECM composition can include differing levels of bioactive agents (e.g. FGF-2) retained from source tissues, thus creating ECM constructs having both density and bioactivity gradients.

In one embodiment, the ECM composition is prepared from expanded or and/or non-expanded ECM source materials processed to form a particulate composition comprising ECM particles differing in their ability to migrate through a fluid medium when subjected to centrifugal force. The ECM particles can differ in size, density, shape, or any or all of these, relative to one another. A particulate composition may be prepared by comminuting an expanded or non-expanded ECM source material. In another embodiment, the ECM composition is prepared by admixing a first population of ECM particles with a second, separately-prepared population of ECM particles, the first population characterized by a first average particle size or first average particle density or first general particle shape, and the second population characterized by a second average particle size or second average particle density or second general particle shape, whereby the corresponding average particle sizes or average particle densities or general particle shapes differ from one another in the first and second populations. One or both of the first and second populations may contain a population of ECM particles that have been expanded in volume by contact with a denaturing agent such as an acid or base.

In another embodiment, a porous, substantially acellular ECM material includes first and second populations of ECM particles cast under centrifugal force in a mold and dried to form a porous, substantially acellular ECM material, characterized by a density gradient extending from a less dense central region to a more dense outer region, or vice versa. The first population of ECM particles is characterized by a first average particle size or first average particle density or a first general particle shape. The second population is characterized by a second average particle size or second average particle density or second general particle shape, such that the corresponding average particle sizes or average particle densities or general particle shapes differ from one another in the first and second populations. The porous, substantially acellular ECM material includes a sufficient amount of expanded ECM particles comminuted from expanded ECM source materials sufficiently treated with a denaturing medium, such as an alkaline medium, so that the porous, substantially acellular ECM material is expandable in an aqueous fluid environment by at least 100% in volume.

DETAILED DESCRIPTION

In order to provide a clear and consistent understanding of the specification and claims, the following definitions are provided.

The term "ECM particle" refers to an ECM particulate derived from a native ECM animal tissue source material processed to from a particle composition or particulate composition.

The term "expanded ECM material" refers to a porous ECM material composition obtained from a non-expanded ECM material treated under conditions that expand the volume of the non-expanded ECM material.

The term "expanded ECM particles" refers to an ECM particle composition obtained by processing an "expanded ECM material" to a particulate composition.

The terms "non-expanded ECM material" and "non-expanded tissue source" are used interchangeably to refer to a material composition processed from a natural ECM animal tissue source material, which has not been exposed to alkaline conditions, acid conditions or other conditions sufficient to substantially disrupt the collagen packing characteristics of the native ECM source material so as to increase its volume.

The term "non-expanded ECM particles" refers to an ECM particle composition comminuted from a "non-expanded ECM material" as described above, to form a particle composition characterized by a particle size, particle size range, density, and/or density range.

In one embodiment, a method for forming an extracellular matrix (ECM) material includes comminuting one or more ECM source materials to form a first composition of ECM particles differing in size, density, shape, or some or all of these characteristics, relative to a second composition of ECM particles. In accordance with certain aspects of the invention, at least one of the first or second compositions includes expanded ECM particles. The ECM particles, including the expanded ECM particle composition are combined in a fluid medium, for example an aqueous liquid medium, to form a flowable ECM composition. The flowable ECM composition is introduced to a mold and subjected to a centrifugal force about an axis of rotation for a period of time sufficient to distribute the ECM particles in the mold according to their ability to migrate through the fluid medium, for example their size, density, shape, or any combination of these. The resulting mold is dried and solidified to form an ECM material having a shape defined by the mold, whereby the dried ECM material is defined by a central longitudinal axis and outer surfaces, such that the ECM particles establish a density gradient in the ECM material characterized by an outer density near an outer surface that is greater than an inner density of the dried ECM material toward the central longitudinal axis.

In certain embodiments, the mold containing the flowable ECM composition is rotated under conditions wherein the entire cross-section of the mold taken in a plane perpendicular to the axis of its rotation remains occupied with at least some depth of the flowable ECM composition during the rotation. In this fashion, an eventual dried ECM material having a cross-section spanning the entire cross-section of the mold perpendicular to the axis of rotation can be obtained. Conditions suitable for these purposes include, for example, filling a closed mold with the flowable ECM composition to such a volume that no practical level of applied centrifugal force will displace all of the ECM composition from the central region of the mold. For example, the ECM composition can be filled to at least about 70% of the volume of a closed mold, or in certain embodiments to at least 80%, at least 90%, or 98-100% of the volume of the closed mold. Conditions for these purposes can also include simply controlling the level of centrifugal force applied so as to retain at least some flowable ECM composition in the central region of the mold while causing the desired migration and distribution of the ECM particles to ultimately form the dried ECM material with a density gradient. Such an operation can be conducted in either a closed or open mold.

In one embodiment, the flowable composition includes expanded ECM particles differing in size, density, shape, or any or all of these, whereby the expanded ECM particles are comminuted from an expanded ECM sheet material(s). By way of example, the expanded ECM sheet material may be comminuted from a processed sheet of dried, substantially acellular ECM tissue source material sufficiently treated with an alkaline medium and crosslinking agents so that the ECM sheet material is expandable in an aqueous fluid environment by at least 100% in volume.

In another embodiment, the flowable composition includes a mixture of expanded ECM particles and non-expanded ECM particles differing in size, density, shape, or any or all of these. Non-expanded ECMs may be formed from native ECM sheet materials processed without alkaline treatment or conditions sufficient to substantially disrupt covalent intramolecular bonds, covalent intermolecular bonds, and/or hydrogen bonds between collagen fibrils so as to alter the structural morphology or collagen packing characteristics of the native ECM source material.

In another embodiment, a method for forming an ECM material includes comminuting one or more ECM materials to form one or more compositions of ECM particles, which are added to a fluid medium to form a flowable ECM composition. One or more portions of a mold are overlaid with a solid ECM material and the flowable ECM composition is introduced thereover. The contents in the mold are subjected to a centrifugal force about an axis of rotation for a period of time sufficient to distribute ECM particles from the flowable ECM composition into the solid ECM material or onto the solid ECM material. The distributed ECM particles in combination with the solid ECM material are dried to form a porous ECM material having a shape defined by the mold, whereby the dried ECM material is defined by a central longitudinal axis and outer surfaces, such that a density of material at an outer surface differs from the density of material in an inner portion of the ECM material. In certain embodiments, the density of the material at an outer surface of the ECM material is greater than a density of material in an inner portion of the ECM material, or vice versa.

In another embodiment, a porous, substantially acellular ECM material includes first and second populations of ECM particles centrifugally cast in a mold and dried to form a porous, substantially acellular ECM material, characterized by a density gradient extending from a less dense region to a more dense region. The less dense region can be a central region while the more dense region is an outer region, or vice versa. The first population of ECM particles is characterized by a first average particle size or first average particle density or first general particle shape. The second population is characterized by a second average particle size or second average particle density or second particle shape, such that the corresponding average particle sizes or average particle densities or second general particle shapes differ from one another in the first and second populations. The porous, substantially acellular ECM material includes a sufficient amount of expanded ECM particles comminuted from expanded ECM source materials, for example sufficiently treated with an alkaline medium and crosslinking agents, so that the porous, substantially acellular ECM material is expandable in an aqueous fluid environment by at least 100% in volume.

In another embodiment, a flowable ECM composition containing expanded ECM particles is cast under centrifugal forces on a solid or sheet-form ECM material overlaid on at least a portion of a mold. The solid ECM material may include expanded ECM materials or non-expanded ECM materials. The expanded ECM particles may include expanded ECM particles differing in size, density, or both. In one embodiment, the solid ECM material includes a non-expanded ECM material, such as a non-expanded ECM outer layer, whereby expanded ECM particles are deposited onto surfaces of the non-expanded ECM material so as to establish a density gradient in the resulting ECM material characterized by an outer density near an outer surface that is greater than an inner density of the dried ECM material toward the central longitudinal axis.

In another embodiment, the solid ECM material includes a porous, expanded ECM material allowing entrapment of ECM particles during the step of casting under the influence of centrifugal force. In this case, the ECM particles may include non-expanded ECM particles, expanded ECM particles, or combinations thereof, whereby the ECM particles may differ in size, density, shape, or any combination or all of these relative to one another so as to establish a density gradient in the material characterized by an outer density near an outer surface that is greater than an inner density of the dried ECM material toward the central longitudinal axis, or vice versa.

The solid ECM material overlaid in the mold is configured to form an outer portion of the resulting cast preparation prepared therein. The solid ECM material may include expanded or non-expanded ECM material, and it may be dry or wet. In particular, the solid ECM material may be in the form of a sheet, solid plug, hollow plug, sleeve, or other material form as defined by the mold. Upon application of a suitable centrifugal force, about an axis of rotation, the ECM particles may become entrapped in a porous expanded ECM material or it may be deposited onto non-expanded ECM material during the casting step. The resulting expanded ECM material is shaped according to the mold, the material comprising a density gradient characterized by an outer density near an outer surface that is greater than an inner density of the dried ECM material toward the central longitudinal axis.

Preparation of ECM Particles From Expanded or Non-Expanded ECM Materials

ECM particles can be prepared by cutting, tearing, grinding, shearing or otherwise comminuting a processed sheet or expanded or non-expanded ECM sheet materials. For example, the source material may be comminuted by shearing the ECM material with a rotating blade, e.g. in a blender.

Expanded ECMs may be formed by controlled contact of ECM sheet materials with an alkaline substance as described below. The ECM sheet materials include one or more naturally-derived ECM tissue layers containing a collagenous ECM scaffold. The ECM sheet material can be in the form of a single tissue layer or a plurality of tissue layers in a laminate, material, or combination thereof.

Expanded and non-expanded ECM sheet materials may be formed from natural ECM source materials, including submucosa-containing tissues, e.g. obtained from small intestinal, stomach or bladder tissue, pericardial tissue, peritoneal tissue, fascia, or dermal tissue, and may include other sheet-form ECM materials described in U.S. Pat. Appl. No. 61/074,441, entitled "Physically Modified Extracellular Matrix Materials and Uses Thereof," filed Jun. 20, 2008, and U.S. Pat. No. 6,206,931, the teachings of which are expressly incorporated by reference herein.

An expanded ECM material for use in the present invention can be processed into a variety of useful forms and materials that are expandable when wetted, so as to achieve an expanded configuration of the ECM when deployed. In one embodiment, the expanded ECM material exhibits a capacity to expand at least 100% by volume, more preferably at least about 200% by volume, and typically in the range of about 300% by volume to about 1000% by volume, when wetted to saturation with deionized water. An expanded ECM material will also exhibit advantageous rates of expansion, achieving volume expansions as noted above in less than about 10 seconds, more preferably less than about 5 seconds, when immersed in deionized water.

Centrifugal Casting of ECM Materials

In one embodiment, a flowable composition containing ECM particles is introduced to a mold or cast to form a mold or cast preparation. By way of example, the mold or cast configuration may be configured in the form of a solid plug, disc, cylindrical-shaped hollow sleeve, or other desirably shaped form. The flowable composition may include expanded ECM particles alone, or it may additionally include non-expanded ECM particles for increased structural integrity, for example in the outer portions of the resulting material, including portions that may be configured for contact with or attachment to one or more tissue portions in a body.

The ECM particles of the present invention may be centrifugally cast in molds subjected to centrifugal forces, generally equivalent to about 5 G to about 3000 G (times the force of gravity), or characterized by rotational velocities between about 2,000 to about 20,000 rpms in general using casting processes, devices, and molds as described in, for example, U.S. Pat. Nos. 4,610,693, 5,292,515, 5,980,792, and 6,787,090, the disclosures of which are incorporated by reference herein.

When subjected to centrifugal force, the suspended ECM particles of varied physical characteristics can be caused to migrate to different extents within the fluid medium, thus providing a distribution of particles that will ultimately provide a density distribution in the dried construct. Additionally, the ECM particle populations in the flowable ECM medium can have varied bioactivity relative to one another (e.g. having differing levels of growth factors, glycosaminoglycans, and/or proteoglycans retained from the source tissue for the particles). Thus, the distributed particles and finished dried constructs can also have a bioactivity gradient. For example, in certain embodiments in which non-expanded ECM particles and expanded ECM particles are used in combination, the non-expanded ECM particles will have a higher content of one or all of a native growth factor (e.g. FGF-2), glycosaminoglycans, or proteoglycans. This will lead to a bioactivity gradient in the finished construct in accordance with the distribution of the non-expanded ECM particles during the centrifugal processing.

Drying and Shaping of ECM Materials

Following and/or during application of the centrifugal forces to distribute the ECM particles in the mold, the wet cast preparation may be dried. In one embodiment, an ECM cast preparation is dried by lyophilization (or freeze drying) either during continued rotation of the cast preparation, or after, or both. In one embodiment, the flowable ECM can be subjected in the mold to both centrifugal force and freezing conditions such that a frozen cast preparation with the desired ECM particle distribution is obtained as the centrifugal force is applied, and such a frozen cast preparation can then be dried under vacuum by sublimation of the water and/or other liquid used to prepare the case.

In other embodiments, the fluid medium used to prepare the flowable ECM composition can be a gellable fluid, and can be caused to gel during or after subjecting the flowable ECM composition to centrifugal force to stabilize the position of the distributed ECM particles. The formed gel construct can then be subjected to lyophilization or other drying conditions as herein described. The fluid medium can be gellable, for example, due to the incorporation of a thermoresponsive gelling agent. The thermoresponsive gelling agent can be one which causes gel formation in response to reduced temperature conditions, for example gelatin. Alternatively, the thermoresponsive gelling agent can cause gel formation in response to increased temperature conditions. As an example, such a gelling agent can include an ECM digest composition comprising solubilized ECM components prepared as described in U.S. patent application Ser. No. 11/851,923 filed Sep. 7, 2007 and published May 8, 2008 as U.S. Patent Application Publication No. 20080107750, the disclosure of which are expressly incorporated by reference herein. The digests exhibit enhanced gelling at 37° C. as compared to ambient temperatures (about 25° C.) and thus can be used to provide a thermoresponsive fluid medium in which the ECM particles are suspended and distributed. The disclosed ECM digests can also include bioactive agents such as FGF-2 from their source tissue, and thus contribute in providing bioactivity to the final construct.

In another embodiment, the ECM cast preparation is dried by vacuum drying at ambient or elevated temperatures during and/or after application of the centrifugal force. Drying the matrix will stabilize its structure and in certain embodiments strengthen the denser matrix portion of the dried material relative to dried materials otherwise lacking a density gradient of ECM particles according to the present invention.

Further, as a result, of the drying procedure, the liquid (e.g. water) content of the matrix may be reduced to less than about 20% by weight, more preferably less than about 10% by weight. The drying process can be applied so as to achieve a final density and/or configuration as desired. For example, an expandable plug can be formed and/or processed (e.g. compressed) having a generally cylindrical shape with a generally circular cross section, and can have a diameter approximating that or smaller than that of a catheter sheath through which it is to be passed.

A dried material can have a shape defined by the mold. By way of example, the cast preparation may be lyophilized to form a dried ECM material in the form of a solid plug, hollow plug, sleeve, or other material having a shape defined by the mold.

In one embodiment, an expanded ECM material is added to a mold or cast to form a molded cast preparation, which is lyophilized to form an expandable plug configured to expand in a fluid environment so as to occlude a body vessel and block fluid flow therethrough. In another embodiment, the molded cast preparation may be lyophilized to form a dried sleeve or hollow tube, which may be associated with or linked to a stent or other medical device.

A shaped material, such as a sleeve or plug may be formed individually by compacting/drying an appropriately sized material, or it may be individually excised from a larger compacted/dried material, for example. In addition, bioactive agent(s) may be exogenously incorporated into the shaped ECM material in support of the material's intended use. Thus, a shaped article such as a sleeve or plug may be formed from ECM materials exogenously incorporating (in their pores, for examples) bioactive agents supporting their intended use. By way of example, the bioactive agent(s) may be incorporated within the pores of the expanded ECM material during processing.

Bioactive agents for use in the present invention may include any agent capable of rendering a beneficial physiological effect in treating, preventing, or reducing the onset of a pathological condition in a subject receiving a medical device, such as one including an ECM-based material of the present invention. More particularly, the bioactive agent may be an organic compound, inorganic compound, synthetic molecule, drug, antiproliferative agent, paclitxel, synthetic polymer, antibiotic, biological polymer, peptide, peptidomimetic, polypeptide, growth factor, antibody, peptide conjugate, nucleic acid, oligonucleotide, polynucleotide, ribozyme, or small interfering RNA (siRNA). In addition, the bioactive agent may have one or more beneficial properties selected from the group consisting of thrombogenic, fibrogenic, angiogenic, antiproliferative, antiscarring, bactericidal, antithrombolytic, antifibrinolytic, fibrin stabilizing, wound healing, fibroblast stimulatory, vascularization promoting, cell and/or tissue attachment promoting, bioremodelable, extracellular matrix promoting, and the like.

Expanded and Non-Expanded ECM Source Materials and Treatments

The inventive method of the present invention includes the use of expanded ECM materials formed by controlled contact with an alkaline substance as described below. In addition, chemical crosslinks may be introduced in the ECM material in an amount sufficient to produce a desired level of resiliency. The chemical crosslinks may be introduced during preparation of the expanded material prior to comminution, or they may be introduced following the process of the centrifugal casting. The introduction of collagen crosslinks, for example with chemical crosslinkers such as glutaraldehyde, carbodimides, or other chemical crosslinkers identified herein, can enhance the resiliency of the expanded ECM materials, and provide sufficiently compressed material for delivery through catheter, needles, and the like. Increased resiliency in turn provides additional compression upon adjacent tissues when the compressed ECM materials are delivered to a body vessel and then allowed to expand in situ in a patient at a site, for example, in which occlusion is desired.

Notably, such treatment can be used to promote substantial expansion (i.e. greater than about 20% expansion) of the extracellular matrix material, which may processed into a variety of useful forms and materials. The expanded extracellular matrix materials for use in the present invention may expand by at least about 2, at least about 3, at least about 4, at least about 5, or even at least about 6 times its original bulk volume. The magnitude of expansion can be regulated by varying the concentration of the alkaline substance, the exposure time of the alkaline substance to the material, and temperature, among others. These factors can be varied to achieve a material having the desired level of expansion, given the disclosures set forth below.

The application of alkaline substances to a source of native extracellular matrix material, as for example, a collagenous animal tissue layer, alters its structural morphology. Extracellular matrix materials are composed of collagen fibrils comprising a quarter-staggered array of tropocollagen molecules formed as a triple helix of comprising three polypeptide chains linked together by covalent intramolecular bonds and hydrogen bonds. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein will not significantly disrupt the intramolecular and intermolecular bonds, but will denature the material so as to provide a processed thickness to an intact collagenous sheet material that is substantially greater (i.e. at least about 20% greater) than, and preferably at least twice the naturally-occurring thickness of, the collagenous animal tissue layer. Microscopic analysis (at 100× magnification) has established that non-expanded ECM materials exhibit a tightly bound collagenous network whereas the same views of an expanded material exhibit a denatured, but still intact, collagenous network reflecting expansion of the material.

Typically, at least a portion of the material will include a dried, expanded ECM material formed from an ECM source material treated with a sufficient quantity of alkaline medium for a sufficient period of time to produce an ECM material expandable in an aqueous fluid environment by at least 120% and to have a tensile strength of less than 50% of that of its corresponding non-expanded extracellular matrix material.

In addition to allowing for expansion of an ECM material, the application of an alkaline substance alters the collagen packing characteristics of the material as well. Altering such characteristics of the material can be caused, at least in part, by the disruption of the tightly bound collagenous network. A non-expanded ECM material having a tightly bound collagenous network typically has a continuous surface that is substantially uniform even when viewed under magnification (e.g. 100× magnification). Conversely, an expanded ECM material typically has a surface—that is quite different in that the surface is typically not continuous but rather presents collagen strands or bundles in many regions that are separated by substantial gaps in material between the strands or bundles. Consequently, an expanded ECM material typically appears more porous than a non-expanded ECM material. Moreover, the expanded ECM material can be demonstrated as having increased porosity, e.g. by measuring its permeability to water or other fluid passage. The more foamy and porous structure of an expanded ECM material can allow the material to be easily cast into a variety of sponge form or foam form shapes for use in the preparation of the occluding body of the present invention. It can further allow for the compression and subsequent expansion of the material, which is useful for purposes of loading a vascular plug device of the present invention into a suitable vascular plug assembly. Once delivered, the material can expand to its original form.

With respect to the alkaline substance used to prepare an expanded ECM material, any suitable alkaline substance generally known in the art can be used. Suitable alkaline substances can include, for example, salts or other compounds that provide hydroxide ions in an aqueous medium. Preferably, the alkaline substance comprises sodium hydroxide (NaOH). The concentration of the alkaline substance that is added to the material can be in the range of about 0.5 to about 4 M. Preferably, the concentration of the alkaline substance is in the range of about 1 to about 3 M. Additionally, the pH of the alkaline substance will typically range from about 8 to about 14. In preferred embodiments, the alkaline substance will have a pH of from about 10 to about 14, and most preferably of from about 12 to about 14.

In addition to concentration and pH, other factors such as temperature and exposure time will contribute to the extent of expansion. In this respect, it is preferred that the exposure of the ECM material to the alkaline substance is performed at a temperature of about 4 to about 45° C. In preferred embodiments, the exposure is performed at a temperature of about 25 to about 37° C., with 37° C. being most preferred. Moreover, the exposure time can range from about several minutes to about 5 hours or more. In preferred embodiments, the exposure time is about 1 to about 2 hours. In a particularly preferred embodiment, the ECM material is exposed to a 3 M solution of NaOH having a pH of 14 at a temperature of about 37° C. for about 1.5 to 2 hours. Such treatment results in the expansion of an ECM material to at least about twice its original volume. As indicated above, these processing steps can be modified to achieve the desired level of expansion.

With regard to expandable plugs, sponges or other constructs as described herein, expansion additives and/or crosslinking can be used to impart desirable compression/re-expansion properties.

In certain embodiments, an expanded ECM material, in any form, or a dried ECM material having a density gradient as herein described, can be crosslinked. An expanded ECM material or an overall dried ECM material containing it can be crosslinked either before or after it is formed into a medical device, or both. Increasing the amount (or number) of crosslinkages within the material or between two or more layers of the material can be used to enhance its strength. However, when a remodelable material is used, the introduction of crosslinkages within the material may also affect its resorbability or remodelability. Consequently, in certain embodiments, an ECM material will substantially retain its native level of crosslinking, or the amount of added crosslinkages within the medical device will be judiciously selected depending upon the desired treatment regime. In many cases, the material will exhibit remodelable properties such that the remodeling process occurs over the course of several days or several weeks. In certain preferred embodiments, the remodeling process occurs within a matter of about 5 days to about 12 weeks. With regard to a substantially porous construct having a density gradient as herein described, e.g. sponge form construct, crosslinking of the construct may promote re-expansion of the construct following compression, e.g. compression to a smaller delivery profile for implantation into a patient through or by a needle, catheter, sheath or other delivery device.

For use in the present invention, introduced crosslinking of an expanded ECM material and/or of the final dried ECM construct containing it may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride (EDC), polyisocyanates, e.g. diisocyanates such as hexamethylene-diisocyanate, ribose or other sugars, acylazide, sulfo-N-hydroxysuccinamide, or polyepoxide compounds, including for example polyglycidyl ethers such as ethylene glycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

In addition to the alkaline treatment and crosslinking, one or more additives may be incorporated into the expanded ECM material and/or dried ECM construct containing it to promote expansion of a compressed material upon absorption of liquid. Any suitable additive can be used. Suitable additives include, for example, salts, such as sodium chloride, sodium acetate, sodium bicarbonate, sodium citrate, calcium carbonate, potassium acetate, potassium phosphate; hydrogel and water-swelling polymers, such as alginate, polyhydroxethyl methacrylate, polyhydroxypropyl methacrylate, polyvinyl alcohol, polyethylene glycol, carboxymethyl cellulose, polyvinyl pyrrolidone; proteins, such as gelatin; acids and bases, such as acetic acid and ascorbic acid; superabsorbing polymers and gelling agents, such as polyacrylic acid, pectin, polygalacturonic acid, polyacrylic acid-co-acrylamide, polyisobutylene-co-maleic acid; monosaccharides, polysaccharides, and derivatives thereof, such as dextran, glucose, fructose" sucrose; sucrose-ester, -sucrose laurate, galactose, chitosan, poly-N-acetyl glucosamine, heparin, hyaluronan, and chrondroitin sulfate; as well as other potential additives, such as guanidine HCl, urea, hydroxyethyl cellulose, sodium cholate, sodium taurocholate, ionic detergents (e.g., SDS), and non-ionic detergents (e.g., Triton). In preferred embodiments, the one or more additives includes a biocompatible salt such as sodium chloride, sodium acetate, or sodium bicarbonate; and/or polyethylene glycol (e.g. MW 6000).

The one or more additives can provide a variety of functions, including promoting expansion of the material once implanted into a patient. For example, a sponge form expanded ECM material or dried ECM construct containing it including one or more additives can be compressed and placed into a delivery device. Compression of the material can allow the material to be more easily transferred through a catheter to a patient. Upon delivery, the material can expand to at least about its original size prior to compression, for example expanding to occupy at least about 80% of its original volume. Such additives can be included in the ECM material to expand the material at a faster rate than would otherwise be achievable in the absence of the one or more additives. For example, one or more additives can be included with a compressed ECM material so as to promote the re-expansion of the material back toward its original size within at least about 30 seconds, 45 seconds, 1 minute, 2 minutes, 3 minutes, 4 minutes, or even about least about 5 minutes after implantation. These additives may be applied to the expanded ECM material as a premanufactured step, immediately prior to the procedure (e.g. by soaking the material in a solution containing the additive(s)), or during or after engraftment of the material in the patient.

Further, the expanded or non-expanded ECMs, or a dried construct including them, can include one or more additives to promote hemostasis. Suitable such additives include, as examples, calcium alginate or zeolite. Such additives can include adhesive properties that allow the ECM material to adhere to a desired location (e.g., tissue surface) after implantation.

The expanded ECM materials or materials for use in the present invention may be freeze-dried by lyophilization. Freezing can be done at a temperature of about −80° C. for about 1 to about 4 hours; and lyophilization can be performed for about 8 to about 48 hours. In addition, the expanded extracellular matrix materials may be comminuted prior to lyophilization. Expanded extracellular matrix materials may be comminuted by shearing the material with a rotating blade, e.g. in a blender. For these purposes, it has been discovered that when utilizing an extracellular matrix material harvested as a decellurized sheet, the sheet can be contacted with the alkaline medium under conditions sufficient to substantially reduce the tensile strength of the sheet, so that the sheet material is disrupted by the rotating blade. Without sufficient reduction of tensile strength by the alkaline medium, the sheet material can tend to wrap around the rotating blade, thus frustrating the process of comminution. Therefore, prior to comminution by the blade or otherwise, the sheet may be desirably treated with the alkaline medium for a time and under conditions sufficient to reduce the tensile strength of the sheet to less than about 50% of its original tensile strength, more preferably to less than about 30% of its original tensile strength. Such methods can be practiced, for example, with harvested sheet-form ECM materials such as submucosa-containing sheets, e.g. obtained from small intestinal, stomach or bladder tissue, pericardial tissue, peritoneal tissue, fascia, dermal tissue, and other sheet-form ECM materials.

In preferred forms, the constructs or expanded ECM materials are capable of volumetric compression when dry at a ratio of at least 10:1 (i.e. the compressed form occupies no more than 10% of its original, relaxed and non-expanded volume), more preferably at a ratio of at least 20:1. At the same time, in preferred forms, the compressed constructs or ECM materials are capable of re-expansion to substantially their original volume (e.g. at least about 80% of their original volume, more preferably at least 90%, and most preferably at least 95%) within about 30 seconds when delivered in their dry and/or compressed form into a volume of water.

A dry, compressed ECM construct can be prepared from density gradient ECM materials described herein. The compressed constructs can be prepared by compressing a formed, porous density gradient ECM material in one, two, or three dimensions, including radially compressing the ECM material (e.g. to form a generally cylindrical compressed construct). Such dry, compressed constructs can have an average density of at least about 0.05 $g/cm^3$, in certain embodiments in the range of about 0.05 $g/cm^3$ to about 0.2 $g/cm^3$, and in certain other embodiments about 0.075 $g/cm^3$ to about 0.2 $g/cm^3$. The dry, compressed construct can be configured to have sufficient rigidity for passage through a catheter sheath during delivery. Expanded plug average densities (dry) will generally be less than the corresponding compacted densities. Average expanded densities (dry) can range from about 0.01 $g/cm^3$ to about 0.1 $g/cm^3$, and in certain embodiments about 0.02 $g/cm^3$ to about 0.07 $g/cm^3$.

The expanded sizes typical for expandable plugs of the present invention include diameters between about 4 mm to about 20 mm, and expanded length between about 4 mm to about 100 mm. Such levels of expansion and final sizes are expected to be capable of exerting compression on surrounding tissues when the ECM construct is implanted, e.g. in a blood vessel such as an artery or vein (e.g. when used for occlusion) or in a wound site (e.g. when used for hemostasis), including for instance a biopsy site.

The expanded ECM source materials for the present invention can be provided in a variety of forms during the processing of ECM materials for use in the present invention. These forms include a flowable aqueous composition (e.g., a fluidized composition), a powder, a gel, a sponge, a foam, one or more sheets, or a cast body.

The expanded and other ECM materials of the present invention may be derived from native ECM animal tissue source materials and/or tissue extracts therefrom as described below. Suitable ECM tissue source materials may be isolated from warm-blooded vertebrate, especially mammals, and may be processed so as to have remodelable properties promoting cellular invasion and ingrowth, as well as biotropic properties promoting angiogenesis, for example. Exemplary ECM tissue source materials include submucosa, renal capsule membrane, dermal collagen, dura mater, pericardium, fascia lata, serosa, and peritoneum or basement membrane layers, including liver basement membrane. These and other similar animal-derived tissue layers can be expanded and processed as described herein. Suitable submucosa materials for these purposes include, for instance, intestinal submucosa, including small intestinal submucosa, stomach submucosa, urinary bladder submucosa, and uterine submucosa.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

When preparing an expanded ECM material, the material is preferably treated with a disinfecting agent so as to produce a disinfected, expanded ECM material. Treatment with a disinfecting agent can be done either prior to or after isolation of the ECM material from the tissue source or can be done either prior to or after expansion. In one preferred embodiment, the tissue source material is rinsed with a solvent, such as water, and is subsequently treated with a disinfecting agent prior to delamination. It has been found that by following this post-disinfection-stripping procedure, it is easier to separate the ECM material from the attached tissues as compared to stripping the ECM material prior to disinfection. Additionally, it has been discovered that the resultant ECM material in its most preferred form exhibits superior histology, in that there is less attached tissue and debris on the surface compared to an ECM material obtained by first delaminating the submucosa layer from its source and then disinfecting the material. Moreover, a more uniform ECM material can be obtained from this process, and an ECM material having the same or similar physical and biochemical properties can be obtained more consistently from each separate processing run. Importantly, a highly purified, substantially disinfected ECM material is obtained by this process. In this regard, one embodiment of the invention provides a method for preparing an expanded ECM material. The method comprises providing a tissue source including an ECM material, disinfecting the tissue source, isolating the ECM material from the tissue source, and contacting the disinfected ECM material with an alkaline substance under conditions effective to expand the ECM material to at least about two times its original volume, thereby forming the expanded ECM material. Upon formation of the expanded ECM material, the material can be further processed into medical materials and/or devices, or can be stored, e.g. in high purity water at 4° C., for later use.

Preferred disinfecting agents are desirably oxidizing agents such as peroxy compounds, preferably organic peroxy compounds, and more preferably peracids. As to peracid compounds that can be used, these include peracetic acid, perpropioic acid, or perbenzoic acid. Peracetic acid is the most preferred disinfecting agent for purposes of the present invention. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa materials as described herein, preferably exhibiting a bioburden of essentially zero and/or essential freedom from pyrogens. In this regard, desirable processes of the invention involve immersing the tissue source or isolated ECM material (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol.

Expanded ECM materials for use in the present invention may be processed from expanded ECM sheet materials or from non-expanded ECM sheet materials treated as described above to form expanded ECM sheet materials. Generally, the ECM sheet materials will have a thickness in the range of about 0.2 mm to about 2 mm, more preferably about 0.4 mm to about 1.5 mm, and most preferably about 0.5 mm to about 1 mm.

A non-expanded source material for preparing an expanded ECM material may include a variety of bioactive components including, for example, one or more of growth factors, glycoproteins, glycosaminoglycans, proteoglycans, nucleic acids, and lipids. Under certain circumstances, treating the source material with an alkaline substance under conditions as described herein may significantly reduce, if not completely eliminate, the bioactivity of these components from the material. Indeed, the treatment of the ECM material with an alkaline substance can result in an ECM material which is substantially devoid of growth factors, glycoproteins, glycosaminoglycans, proteoglycans, nucleic acids, and lipids. Accordingly, the treatment of an ECM material with an alkaline substance as described herein can cause the material to expand to at least about twice its original volume, can alter the surface and/or porosity characteristics of the material, and can deplete the material of certain bioactive components.

In some embodiments, a sheet of ECM material may be treated with the alkaline medium so as to expand it as described herein, while retaining an amount of a growth factor such as FGF-2, or another bioactive component such as fibronectin and/or glycosaminoglycans (e.g. heparin), that is/are native to the source tissue for the ECM- or other collagenous materials.

In other embodiments, selected bioactive components that were previously removed from the ECM material can be returned to the material. For example, the present invention can provide an expanded ECM material or a density gradient ECM construct prepared including it, which is substantially devoid of nucleic acids and lipids, but which has been replenished with one or more growth factors, glycoproteins, glycosaminoglycans, or proteoglycans or combinations thereof. These bioactive components can be returned to the material by any suitable method. For instance, in certain forms, a tissue extract containing these components can be prepared and applied to an expanded ECM material or the density-gradient ECM construct or another precursor thereto. In one embodiment, the expanded ECM material or ECM construct may be incubated in a tissue extract for a sufficient time to allow the bioactive components contained therein to associate with the material. The tissue extract may, for example, be obtained from non-expanded remodelable collagenous tissue of the same type used to prepare the expanded material. Other means for returning or providing bioactive components to an expanded ECM material or ECM construct include spraying, impregnating, dipping, etc. as known in the art.

By way of example, an expanded ECM material or an ECM construct containing it may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). These growth factors may be prepared from cell or tissue extracts, or they may be synthetically produced by recombinant technology. As well, an expanded ECM material or an ECM construct may be replenished with other biological components such as heparin, heparin sulfate, hyaluronic acid, fibronectin and the like. Thus, generally speaking, an expanded ECM material or an ECM construct may include a bioactive component that induces, directly or indirectly, a cellular response such as a change in cell morphology, proliferation, growth, protein or gene expression.

The preparation of submucosa extracts is described in, for example, U.S. Pat. No. 6,375,989. Briefly, a submucosa extract can be prepared by the addition of an extraction excipient, such as urea, guanidine, sodium chloride, magnesium chloride, or a surfactant, to a submucosa tissue to isolate bioactive components—from the tissue. The bioactive components are then separated from the extraction excipient. In one preferred embodiment, a submucosa extract is prepared by mixing submucosa tissue with a phosphate buffered solution, such as phosphate buffered saline (PBS). This mixture is processed into a slurry as buffer circulation and physical pressure are applied. The bioactive components present in the tissue are drawn into solution and subsequently isolated from the slurry. The bioactive submucosa extract is then formed by separating the extracted bioactive components in the solution from the slurry using art-recognized procedures such as dialysis and/or chromatographic techniques. Preferably, the extraction solution is dialyzed to reduce or remove the concentration of extraction excipients to provide a solution of the extracted bioactive components. Any source of submucosa tissue can be used to prepare a submucosa extract. Moreover, similar extraction techniques can be applied to other remodelable ECM materials to provide biologically active extracts for use in the invention.

The nature and quantity of the bioactive components contained in the submucosa or other ECM extract is dependent on the nature and composition of the extraction excipients used for the extraction solution. Thus, for example, 2 M urea in a pH 7.4 buffer provides an extracted submucosa fraction enriched for basic fibroblast growth factor and fibronectin, while 4 M guanidine in the same buffer provides an extracted submucosa fraction enriched for a compound exhibiting an activity profile for TGF-beta. Use of other extraction excipients provides bioactive extracts comprising proteoglycans, glycoproteins and glycosaminoglycans such as heparin, heparin sulfate, hyaluronic acid, chondroitin sulfate A and chondroitin sulfate B.

In addition to, or as an alternative to the inclusion of native bioactive components, such as those provided in a submucosa or other ECM extract, non-native bioactive components including those synthetically produced by recombinant technology or other methods, may be incorporated into the expanded ECM material. These non-native bioactive components may be naturally-derived or recombinantly produced proteins that correspond to those natively occurring in the ECM tissue, but perhaps of a different species (e.g. human proteins applied to collagenous ECMs from other animals, such as pigs).

In addition, non-native bioactive agents may be incorporated into the expanded ECM materials or ECM constructs. Bioactive agents for use in the present invention may include, for example, any agent capable of promoting occlusion or stable engraftment or integration of the ECM material into a patient's body tissue(s). The bioactive agent may be an organic compound, inorganic compound, synthetic molecule, drug, antiproliferative agent, paclitxel, synthetic polymer, antibiotic, biological polymer, peptide, peptidomimetic, polypeptide, growth factor, antibody, peptide conjugate, nucleic acid, oligonucleotide, polynucleotide, ribozyme, or small interfering RNA (siRNA).

In addition, the bioactive agent may have one or more beneficial properties having thrombogenic, fibrogenic, angiogenic, antiproliferative, bactericidal, wound healing, fibroblast stimulatory, vascularization promoting, cell and/or tissue attachment promoting, bioremodeling, blood clotting, ECM-promoting agents, and the like.

Additional expanded ECM compositions for use in the expanded ECM materials of the present invention, including methods for making these compositions are described in U.S. patent application Ser. No. 12/488,996, entitled "Composite Extracellular Matrix Materials and Medical Products Formed Therefrom," filed Jun. 22, 2009, and U.S. patent application Ser. No. 12/488,974, entitled "Compressible/Expandable Medical Graft Products, and Methods for Applying Hemostasis," filed Jun. 22, 2009, the disclosures of which are expressly incorporated by reference herein.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for forming an extracellular matrix (ECM) material comprising:
   a. providing an ECM composition containing ECM particles, the ECM particles including a first population of ECM particles and a second population of ECM particles, the first and second populations of ECM particles having different respective abilities to migrate through a fluid medium, wherein the first population comprises expanded ECM particles and the second population comprises non-expanded ECM particles;
   b. forming a flowable ECM composition including the ECM particles and the fluid medium;
   c. subjecting the flowable ECM composition to a centrifugal force in a mold for a period of time sufficient to distribute the first and second populations of ECM particles in the mold according to their respective abilities to migrate through the fluid medium; and
   d. drying the ECM composition to form a dried ECM material having a density gradient extending from a less dense region to a more dense region.

2. The method of claim 1, wherein the dried ECM material is defined by a central longitudinal axis and by outer surfaces, wherein the ECM particles establish a density gradient in the ECM material characterized by an outer density near the outer surfaces that is greater than an inner density of the dried ECM material toward the central longitudinal axis.

3. The method of claim 1, wherein the ECM composition is prepared from an ECM source material processed to form a particulate composition comprising ECM particles differing in size, density, shape, or combination thereof relative to one another.

4. The method of claim 1, wherein the ECM composition is prepared by admixing a first population of expanded ECM particles with a second, separately prepared population of non-expanded ECM particles, wherein the first expanded population is characterized by a first average particle size, first average particle density, first general particle shape, or combination thereof, and the second non-expanded population is characterized by a second average particle size, second average particle density, second general particle shape, or combination thereof, wherein the corresponding average particle sizes, average particle densities or average general particle shapes differ from one another in the first and second populations.

5. The method of claim 1, wherein the expanded ECM particles in the flowable composition are formed from an ECM tissue source material sufficiently treated with an alkaline medium and crosslinking agents, so that when added to the flowable composition in sufficient amounts, the dried ECM material will be expandable in an aqueous fluid environment by at least 100% in volume.

6. The method of claim 1, wherein the ECM composition is dried by lyophilization.

7. The method of claim 1, wherein the flowable composition is introduced to the mold to form a porous, substantially acellular ECM material.

8. The method of claim 1, wherein the ECM material is formed into a solid plug, hollow plug or sleeve.

9. The method of claim 1, also comprising freezing the flowable ECM composition during said subjecting step to form a frozen cast structure, and sublimation drying the cast structure under vacuum.

10. The method of claim 1, wherein the fluid medium is a gellable medium, and the fluid medium is caused to gel during and/or after said subjecting step.

11. The method of claim 10, wherein the fluid medium includes a thermoresponsive gelling agent.

12. The method of claim 11, wherein the thermoresponsive gelling agent causes the fluid medium to gel in response to reduced temperature conditions.

13. The method of claim 11, wherein the thermoresponsive gelling agent causes the fluid medium to gel in response to increased temperature conditions.

14. An ECM material formed by the method of claim 1.

* * * * *